United States Patent
McBride et al.

(10) Patent No.: US 11,631,037 B2
(45) Date of Patent: Apr. 18, 2023

(54) APPARATUS, SYSTEM AND METHOD FOR PREDICTING MEDICAL NO-SHOWS AND FOR SCHEDULING

(71) Applicant: Mend VIP, Inc., Orlando, FL (US)

(72) Inventors: Matthew McBride, Orlando, FL (US); Brandon Lassiter, Orlando, FL (US); Paul Senzee, Apopka, FL (US); Zach Firestone, Orlando, FL (US); Nils Elde, Longwood, FL (US)

(73) Assignee: Mend VIP, Inc., Orlando, FL (US)

( * ) Notice: Subject to any disclaimer, the term of this patent is extended or adjusted under 35 U.S.C. 154(b) by 71 days.

(21) Appl. No.: 16/825,307

(22) Filed: Mar. 20, 2020

(65) Prior Publication Data
US 2020/0302358 A1    Sep. 24, 2020

Related U.S. Application Data

(60) Provisional application No. 62/821,005, filed on Mar. 20, 2019.

(51) Int. Cl.
*G06Q 10/06*        (2012.01)
*G06N 3/08*         (2006.01)
(Continued)

(52) U.S. Cl.
CPC ......... *G06Q 10/06312* (2013.01); *G06N 3/08* (2013.01); *G06Q 10/063116* (2013.01); *G16H 10/60* (2018.01); *G16H 40/20* (2018.01)

(58) Field of Classification Search
CPC .. G06N 20/00; G06N 3/08; G06Q 10/063116; G06Q 10/06312; G16H 10/60; G16H 40/20
See application file for complete search history.

(56) References Cited

U.S. PATENT DOCUMENTS

| | | | |
|---|---|---|---|
| 2010/0106517 A1* | 4/2010 | Kociubinski | G16H 40/20 705/2 |
| 2015/0242819 A1* | 8/2015 | Moses | G06N 5/04 705/7.19 |

(Continued)

FOREIGN PATENT DOCUMENTS

KR    20190106609 A  *  9/2019  ............. G06Q 10/02

OTHER PUBLICATIONS

"Appointment Scheduling Under Patient No-shows and service Interruptions", by Luo et al., Dependent of Statistics and Operations Research, University of North Caroline at Chapel Hill, NC 27599. Published online in Articles in Advance Jul. 13, 2012. (Year: 2012).*

(Continued)

*Primary Examiner* — Pan G Choy
(74) *Attorney, Agent, or Firm* — Maier & Maier, PLLC

(57) ABSTRACT

A System, Method, and Apparatus for Predicting Medical No-Shows and for Scheduling is provided. The system is based on a patient appointment schedule and indicators including office type, practice area, appointment type, engagement with the office leading up to appointment, and a variety of other characteristics of each patient and appointment. The indicators can be selected, weighted proportionately, and input into an algorithm for analysis and processing. The algorithm can then predict the likelihood of a no-show for the respective patient and appointment. The likelihood can then be used for scheduling to minimize the negative impact on the medical professional of the no-show. The algorithm can be used in conjunction with machine learning to improve its accuracy as it informs itself with experience and additional data points. The likelihood of a no-show can be incorporated into scheduling programs and (Continued)

made accessible on mobile devices, computers, and other monitoring devices.

15 Claims, 2 Drawing Sheets

(51) Int. Cl.
*G16H 10/60* (2018.01)
*G16H 40/20* (2018.01)
*G06Q 10/0631* (2023.01)

(56) References Cited

U.S. PATENT DOCUMENTS

| | | | | |
|---|---|---|---|---|
| 2016/0253462 | A1* | 9/2016 | Zhong | G06Q 10/1095 |
| | | | | 705/2 |
| 2016/0292369 | A1* | 10/2016 | Lakare | G16Z 99/00 |
| 2018/0174079 | A1* | 6/2018 | Choi | G06Q 30/0254 |
| 2018/0218337 | A1* | 8/2018 | Polatov | G06Q 10/1095 |
| 2020/0160986 | A1* | 5/2020 | Vegas Santiago | G06N 20/00 |
| 2020/0294640 | A1* | 9/2020 | Ginsburg | G16H 40/20 |

OTHER PUBLICATIONS

"Can what we learned about reducing no-shows in our clinic work for you?" by Prashant Gajwani, MD, Department of Psychiatry, The university of Texas Health Sciences Center at Houston, Houston, Texas. Current Psychiatry, vol. 13, No. 9, Sep. 2014. (Year: 2014).*
"A Probabilistic Model for Predicting the Probability of No-show in hospital appointments", by Adel Alaeddini, Kai Yang, Chandan Reddy and Susan Yu. Health Care Manag Sci (2011) 14:146-157. Springer Science + Business Media, LLC 2011. (Year: 2011).*

* cited by examiner

APPARATUS, SYSTEM AND METHOD FOR PREDICTING MEDICAL NO-SHOWS AND FOR SCHEDULING

CROSS-REFERENCE TO RELATED APPLICATIONS

This application claims priority from U.S. Provisional Patent Application No. 62/821,005, filed on Mar. 20, 2019, entitled "APPARATUS, SYSTEM AND METHOD FOR PREDICTING MEDICAL NO-SHOWS AND FOR SCHEDULING," the entire contents of which are hereby incorporated by reference.

BACKGROUND

In the medical industry, time and efficiency are at a premium to maximize the number of patients who can be helped and the value of care that professionals can provide to them. These competing goals of time spent on each patient place a tremendous amount of importance on effective appointment scheduling to balance the medical process. Few things can disrupt that balance more than no-show patients. No-shows can lead to wasted time for the professionals, short notice to other patients who might miss that opportunity to see the medical provider, or undue delays to other patients. Some medical professionals try to resolve this by overbooking their patients, thinking that not all will show up and the result would be an approximately maximal schedule. Unfortunately, this solution is not ideal because the specific patients who do not show, the time of their appointment, and even the number of no-shows in total may not align correctly, causing rushed appointments, late appointments, and other systemic issues to the process. Other solutions involve fees for missed appointments in order to minimize the financial loss to the professional for wasted time, but these fees do not resolve the fact that some patients who might otherwise have been able to be helped in that slot cannot be on short notice, and the professional would still waste time that could be better used to serve their patients who do end up showing up. Some attempts have been made to predict no-shows, but they rely too heavily on historical data, without taking necessary indicators like engagement with the office into account and fall short of reliable accuracy. These solutions are quite simply inadequate for the task of maximizing the valuable time that medical professionals have to spend.

SUMMARY

Exemplary embodiments described herein can provide various systems, methods, and apparatuses for predicting medical no-shows and for scheduling. The system is based on indicators for each patient including office type, practice area, appointment type, engagement with the office leading up to appointment, and a variety of other characteristics of each patient and appointment. The indicators can be selected, weighted proportionately, and input into an algorithm for analysis and processing. The algorithm can then predict the likelihood of a no-show for the respective patient and appointment. The likelihood can then be used for scheduling to minimize the negative impact on the medical professional of the no-show. The algorithm can be used in conjunction with machine learning to improve its accuracy as it informs itself with experience and additional data points. The likelihood of a no-show can be incorporated into scheduling programs and made accessible on mobile devices, computers, and other monitoring devices.

BRIEF DESCRIPTION OF THE FIGURES

Advantages of embodiments of the present invention will be apparent from the following detailed description of the exemplary embodiments thereof, which description should be considered in conjunction with the accompanying drawings in which like numerals indicate like elements, in which.

DETAILED DESCRIPTION

Aspects of the invention are disclosed in the following description and related drawings directed to specific embodiments of the invention. Alternate embodiments may be devised without departing from the spirit or the scope of the invention. Additionally, well-known elements of exemplary embodiments of the invention will not be described in detail or will be omitted so as not to obscure the relevant details of the invention. Further, to facilitate an understanding of the description discussion of several terms used herein follows.

As used herein, the word "exemplary" means "serving as an example, instance or illustration." The embodiments described herein are not limiting, but rather are exemplary only. It should be understood that the described embodiments are not necessarily to be construed as preferred or advantageous over other embodiments. Moreover, the terms "embodiments of the invention", "embodiments" or "invention" do not require that all embodiments of the invention include the discussed feature, advantage or mode of operation.

Further, many embodiments are described in terms of sequences of actions to be performed by, for example, elements of a computing device. It will be recognized that various actions described herein can be performed by specific circuits (e.g., application specific integrated circuits (ASICs)), by program instructions being executed by one or more processors, or by a combination of both. Additionally, these sequence of actions described herein can be considered to be embodied entirely within any form of computer readable storage medium having stored therein a corresponding set of computer instructions that upon execution would cause an associated processor to perform the functionality described herein. Thus, the various aspects of the invention may be embodied in a number of different forms, all of which have been contemplated to be within the scope of the claimed subject matter. In addition, for each of the embodiments described herein, the corresponding form of any such embodiments may be described herein as, for example, "logic configured to" perform the described action.

According to an exemplary embodiment, and referring generally to the Figures, various exemplary implementations of an Apparatus, System, and Method for Predicting Medical No-Shows and for Scheduling may be disclosed.

Figure 1:
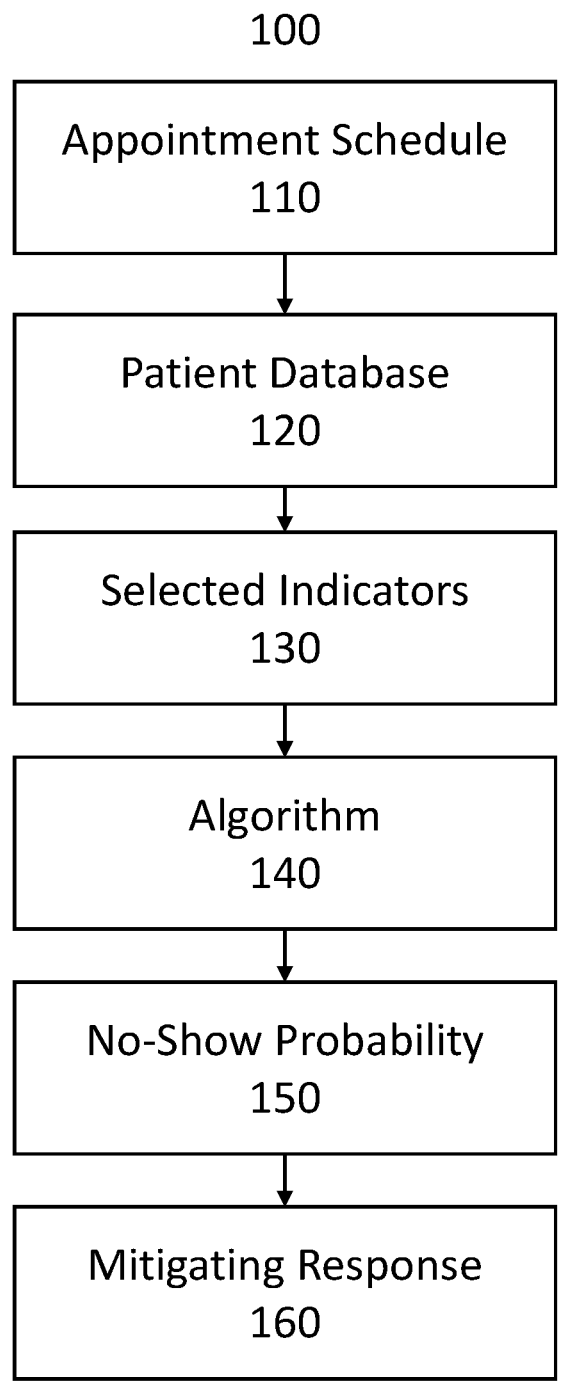
FIG. 1 is an exemplary embodiment of a Method for Predicting Medical No-Shows and for Scheduling.

Turning now to exemplary FIG. 1, FIG. 1 displays an exemplary embodiment of a Method for Predicting Medical No-Shows and for Scheduling. A Method for Predicting Medical No-Shows and for Scheduling 100 may include an Appointment Schedule 110, a Patient Database 120, Selected Indicators 130, an Algorithm 140, a No-Show Probability 150, and a Mitigating Response 160. In an exemplary embodiment, an office may have an appointment schedule 110. The appointment schedule 110 may identify patients for each scheduled appointment. The patient database 120 may include data about each patient in the appointment schedule 110. These datasets may optionally include demographics about the patients, the patients' engagement with the office leading up to the appointment, the practice area of the office and the type of appointment scheduled, the time elapsed since the patients' previous appointment, payment and insurance history for the patients, the cost of the appointment, previous appointments and whether the patients showed up, weather during previous appointments, transportation methods used by the patients, referral source and history, the symptoms and reasons for scheduling the appointments, who scheduled the appointments, diagnoses of the patients, day/week/month of previous appointments, lead time until appointments, types and timing of reminders for appointments given and whether they were received and engaged with, and any other available information about the patient history. Patient demographics may include age, gender, ethnicity, employment, marital status, education level, and any other recordable information about the patient. The patients' engagement with the office leading up to the appointment may optionally include opting in and out of email, voice and SMS phone reminders, whether the reminders were deliverable, whether they responded to reminders as prompted with a response through a keypad, answering a call, opening an email, adding an event to their calendar, confirming an appointment, whether they tested their video connection for video appointments, and any other traceable activity. Selected indicators 130 may be taken from the patient database 120. The selected indicators 130 may be weighted proportionately depending on how relevant they are to a no-show. The selected indicators 130 may be weighted differently depending on the office type, appointment type, practice area, office location, individual doctor, or any other factor. The selected indicators 130 may be input into an algorithm 140.

The algorithm 140 may calculate the likelihood of a no-show based on the selected indicators 130 for a particular patient and appointment. The likelihood of a no-show produced by the algorithm 140 may be a no-show probability 150. The selected factors 130 may be weighted differently based on the data present. The selected factors 130 may be further adjusted based on future appointments and historical appointment comparisons. The algorithm 140 may automatically run regularly. The algorithm may run monthly, weekly, daily, or multiple times per day. The algorithm may run according to a pre-set schedule or when manually prompted. The no-show probability 150 may indicate the confidence rating that the patient will or will not show up to the appointment. The no-show probability 150 may be a numerical percentage out of 100.

In one exemplary embodiment, algorithm 140 may take the form of a summation of each selected factor 130 as scaled by each associated weighting factor. For example, information pertaining to a patient's past attendance history may advantageously be represented in the patient database as a percentage, which may be directly used as by the algorithm 140. However, each selected factor 13 may not be in a format directly useable with the corresponding patient information as stored in the patient database 120. For example, information pertaining to the weather conditions during a patient's past appointment may advantageously be stored as an enumerated value, category, or character string. Or, information pertaining to the nature of a patient's past appointment may be stored using medical coding or clinical coding as is common to medical practice or medical record keeping and known to that art. In these instances, it may be necessary to convert such an enumeration or coding to a patient arrival probability within the algorithm 140. These conversions may be specified by a user or may come pre-loaded in the system. These conversions may be represented as static, but the conversions are preferably dynamic.

The no-show probability 150 may then be communicated to the user. The no-show probability may be shown in one or more manners for the user's use. The no-show probability may be communicated numerically or as a categorical representation. Categorical representations may correspond to the level or levels of likelihood that the patient will show-up. Categories may include a patient being "Highly Likely", "Likely", "Neutral", "Unlikely", or "Highly Unlikely" to show up to their scheduled appointment. The user may be shown both the no-show probability 150 and the selected factors 130 that have resulted in that calculated result. In some embodiments, the no-show probability 150 may be represented with coloring on an appointment calendar. The color on a calendar may be green if the no-show probability 150 is below a certain threshold and the patient is considered "Highly Likely" to show-up. The color on a calendar may be yellow is the no-show probability 150 is at an intermediate level considered "Neutral". The color on a calendar may red if the no-show probability exceeds a certain threshold for the patient to be considered "Highly Unlikely" to show up.

In other embodiments, the no-show probability may appear as an icon on an appointment list. The icons may correspond to categorical representation of a patient's likelihood of showing up to an appointment. In another alternate embodiment, the no-show probability 150 may be expressed as a daily, weekly, monthly, or otherwise regularly provided summary list of all the appointments whose patients are considered to be highly unlikely to show up, highly likely to show up, or any other categorical division based on user preference. A summary list may instead be generated for a specific adjustable date range entered manually.

No-show probability 150 may optionally be tied to an alert. The alert may be activated when the confidence level of a patient showing up goes below a numerical or categorical level. The alert may be auditory or visual. The alert may be integrated into a scheduling program, available on a mobile device, or other means of notification. Based on the no-show probability 150, a scheduler may take a Mitigating Response 160. The mitigating response 160 may include one or more actions based on the no-show probability 150. The mitigating response 160 may include a change in the scheduling to minimize the potential risk. The mitigating response 160 may include a reminder to the patient or a request for confirmation from the patient or other means to reduce the risk of a no-show. The mitigating response 160 may instead an additional appointment being scheduled for the appointment time if the patient is unlikely to show up. The mitigating response 160 may limit additional patients being scheduled to instances where the patient fails to confirm their appointment. The mitigating response 160 may be taken manually by a scheduler or user or may be automatic based on specific factors and/or user preference.

Figure 2:
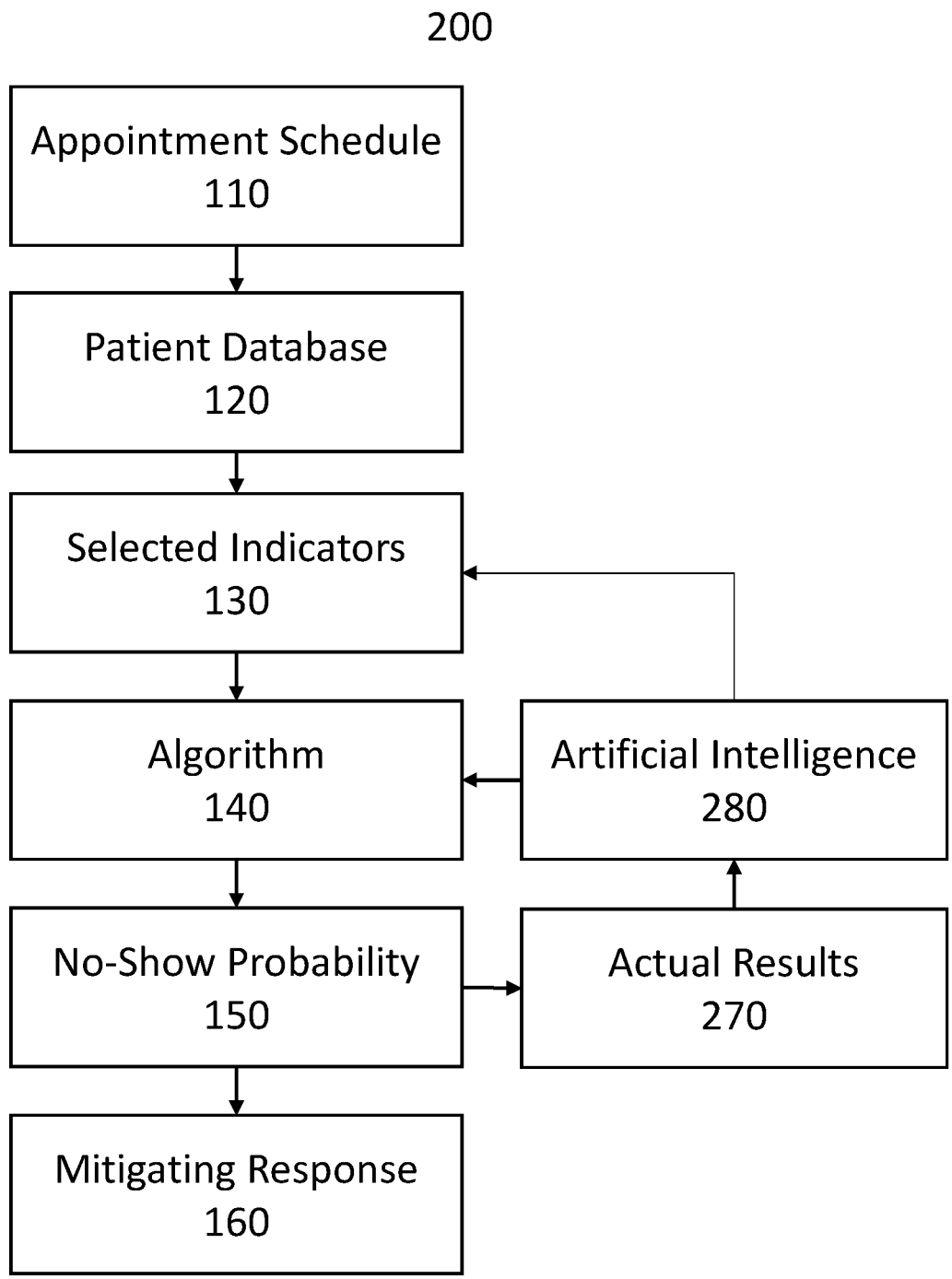
FIG. 2 is an exemplary embodiment of a Method for Predicting Medical No-Shows and for Scheduling with Integrated Artificial Intelligence.

Turning now to exemplary FIG. 2, FIG. 2 displays an exemplary embodiment of a Method for Predicting Medical No-Shows and for Scheduling with Integrated Artificial Intelligence 200. A Method for Predicting Medical No-Shows and for Scheduling with Integrated Artificial Intelligence may be comprised of an Appointment Schedule 110, a Patient Database 120, Selected Indicators 130, an Algorithm 140, a No-Show Probability 150, a Mitigating Response 150, Actual Results 270, and Artificial Intelligence 280. Once a No-Show Probability 150 has been generated and the appointment has passed with either a no-show or a successful appointment, the method 200 may then compare the actual results 270 of each appointment with the no-show probability 150. This comparison may be used by Artificial Intelligence (AI) 280 to improve the accuracy or efficiency of method 200 in further use. AI 280 may use machine learning to inform the chosen selected indicators 120. AI 280 may optionally use machine learning to adjust the algorithm 140. AI 280 may adjust method 200 in any other means including the weighting of indicators, or any combination of changes that may improve the accuracy of method 200.

AI 280 may be trained utilizing reinforcement learning to determine a preferred set of parameters by which the algorithm 140 is to operate. This training may be conducted in a supervised manner by using actual historical data contained within the patient database 120. An exemplary training regime may involve presenting historical data contained within the patient database 120 for each appointment to the AI 280, while purposely excluding information as to whether or not a patient actually attended the appointment—the actual results 270. The AI then, using the algorithm 140, calculates the no-show probability for the patient for a given appointment. This no-show probability is then compared against whether the patient actually attended the appointment, and an accuracy score is correlated to that iteration of the algorithm 140. This accuracy score is then fed back into the reinforcement learning process to optimize the algorithm 140.

It is of note that the algorithm 140 used by the AI 280 in this reinforcement learning process may be the actual algorithm 140 or an approximation or model of the algorithm 140 as is appropriate for the training process. The AI may thus optimize the algorithm 140 or approximation thereof on the basis of determining a preferred set of selected indicators 130 for consideration by the algorithm 140, a preferred set of weights by which each selected indicator 130 may be scaled, and/or an effective conversion metric by which data stored in the patient database 120 may be converted to a more ready form as a selected indicator 130.

The foregoing description and accompanying figures illustrate the principles, preferred embodiments and modes of operation of the invention. However, the invention should not be construed as being limited to the particular embodiments discussed above. Additional variations of the embodiments discussed above will be appreciated by those skilled in the art (for example, features associated with certain configurations of the invention may instead be associated with any other configurations of the invention, as desired).

Therefore, the above-described embodiments should be regarded as illustrative rather than restrictive. Accordingly, it should be appreciated that variations to those embodiments can be made by those skilled in the art without departing from the scope of the invention as defined by the following claims.

What is claimed is:
1. A system for predicting medical no-shows, comprising:
an appointment schedule;
a patient database, which contains patient information associated with each of a plurality of patients;
a machine learning algorithm; and
a processor and non-transitory computer readable storage medium configured to execute instructions which determine a no-show probability, wherein:
the processor uses the appointment schedule to identify one of the plurality of patients stored in the patient database for a scheduled appointment;
the machine learning algorithm is trained via reinforcement learning using historical patient data comprising at least one of a patient's actual attendance rate;
the machine learning algorithm determines which selected indicators out of all possible selected indicators are to be used in calculating the no-show probability;
the no-show probability of an identified patient for the scheduled appointment is determined based on at least one selected indicator which corresponds to the patient information of the identified patient;
each of the at least one selected indicators are weighted by a metric;
the at least one selected indicator comprises at least a measurement of the identified patient's engagement with a reminder;
the machine learning algorithm adjusts the metric used to weight each of the at least one selected indicators;
a mitigating response is automatically performed based on a comparison between the no-show probability and a predetermined threshold, the mitigating response comprising at least one of:
a visual alert generated and displayed on a user interface of a user device, and
an audible alert generated through a speaker of the user device; and
the machine learning algorithm is updated based on a comparison between (1) the no-show probability determined and (2) whether the identified patient showed up to the scheduled appointment.

2. The system for predicting medical no-shows of claim 1, wherein the mitigating response comprises changing a scheduling of at least one patient appointment in the appointment schedule.

3. The system for predicting medical no-shows of claim 1, wherein the mitigating response comprises sending the patient identified for the scheduled appointment a reminding message for the scheduled appointment.

4. The system for predicting medical no-shows of claim 3, wherein the reminder message is sent via email, SMS, or text messaging.

5. The system for predicting medical no-shows of claim 1, wherein the mitigating response comprises allowing an appointment for another patient to be scheduled at the same time as the scheduled appointment.

6. The system for predicting medical no-shows of claim 1, wherein the selected indicators corresponding to patient information further comprise at least one of:
a patient's demographics;
the patient's engagement history with an office leading up to the scheduled appointment;
a practice area of the office;
a type of appointment scheduled;
payment and/or insurance history of the patient;
the patient's actual attendance rate of past appointments;
scheduling information pertaining to the patient's past appointments;
weather conditions during past appointments;
an identifier relating to who scheduled the appointment;
transportation commonly used by the patient;
diagnoses of the patient.

7. The system for predicting medical no-shows of claim 1, wherein the no-show probability is calculated according to a predetermined schedule.

8. The system according to claim 1, wherein the measurement of the identified patient's engagement with the reminder comprises at least one of:
   a decision to opt in or out of email, voice, and/or SMS reminders;
   whether the reminder was deliverable;
   whether the reminder was responded to;
   whether the scheduled appointment was confirmed by the identified patient;
   whether the scheduled appointment was added to a personal calendar of the identified patient; and
   whether the identified patient tested their video connection in advance of a video appointment.

9. A method for predicting medical no-shows performed by a processor of a computing device, comprising:
   identifying a scheduled appointment from an appointment schedule;
   identifying one of a plurality of patients stored in a patient database containing information pertaining to each of the plurality of patients, the identified patient corresponding to the scheduled appointment;
   training a machine learning algorithm via reinforcement learning using historical patient data comprising at least one of a patient's actual attendance rate;
   using the machine learning algorithm to determine which selected indicators out of all possible selected indicators are to be used in calculating a no-show probability;
   computing a no-show probability of the identified patient for the scheduled appointment based on at least one selected indicator which corresponds to the patient information of the identified patient; and
   generating a mitigating response automatically based on a comparison between the no-show probability and a predetermined threshold, the mitigating response comprising at least one of:
      generating and displaying a visual alert on a user interface of a user device, and
      generating an audible alert through a speaker of the user device, wherein:
   each of the at least one selected indicators are weighted by a metric;
   the at least one selected indicator comprises at least a measurement of the identified patient's engagement with a reminder;
   the machine learning algorithm adjusts the metric used to weight each of the at least one selected indicators; and
   the machine learning algorithm is updated based on a comparison between (1) the no-show probability computed and (2) whether the identified patient showed up to the scheduled appointment.

10. The method for predicting medical no-shows of claim 9, wherein the mitigating response comprises changing a scheduling of at least one patient appointment in the appointment schedule.

11. The method for predicting medical no-shows of claim 9, wherein the mitigating response comprises sending the patient identified for the scheduled appointment a reminding message for the scheduled appointment.

12. The method for predicting medical no-shows of claim 9, wherein the mitigating response comprises allowing an appointment for another patient to be scheduled at the same time as the scheduled appointment.

13. The method according to claim 9, wherein the measurement of the identified patient's engagement with the reminder comprises at least one of:
   a decision to opt in or out of email, voice, and/or SMS reminders;
   whether the reminder was deliverable;
   whether the reminder was responded to;
   whether the scheduled appointment was confirmed by the identified patient;
   whether the scheduled appointment was added to a personal calendar of the identified patient; and
   whether the identified patient tested their video connection in advance of a video appointment.

14. A non-transitory computer-readable storage medium containing instructions executable by a processor in order to predict medical no-shows, the instructions configured to:
   identify one of a plurality of patients stored in a patient database, the patient database containing patient information associated with each of the plurality of patients;
   retrieve from an appointment schedule a scheduled appointment which corresponds to the identified patient;
   train a machine learning algorithm via reinforcement learning using historical patient data comprising at least one of a patient's actual attendance rate;
   use the machine learning algorithm to determine which selected indicators out of all possible selected indicators are to be used in calculating a no-show probability;
   compute the no-show probability of the identified patient for the scheduled appointment based on at least one selected indicator which corresponds to the patient information of the identified patient; and
   automatically generate a mitigating response based on a comparison between the no-show probability and a predetermined threshold, the mitigating response comprising at least one of:
      a visual alert displayed on a user interface of a user device, and
      an audible alert generated through a speaker of the user device, wherein:
   each of the at least one selected indicators are weighted by a metric;
   the at least one selected indicator comprises at least a measurement of the identified patient's engagement with a reminder;
   the machine learning algorithm adjusts the metric used to weight each of the at least one selected indicators; and
   the machine learning algorithm is updated based on a comparison between (1) the no-show probability computed and (2) whether the identified patient showed up to the scheduled appointment.

15. The non-transitory computer-readable storage medium containing instructions according to claim 14, wherein the measurement of the identified patient's engagement with the reminder comprises at least one of:
   a decision to opt in or out of email, voice, and/or SMS reminders;
   whether the reminder was deliverable;
   whether the reminder was responded to;
   whether the scheduled appointment was confirmed by the identified patient;
   whether the scheduled appointment was added to a personal calendar of the identified patient; and
   whether the identified patient tested their video connection in advance of a video appointment.

* * * * *